United States Patent [19]

Dalton et al.

[11] 4,276,196
[45] Jun. 30, 1981

[54] ATTRITION RESISTANT CATALYSTS

[75] Inventors: Charles A. Dalton; William E. Slinkard, both of Corpus Christi, Tex.

[73] Assignee: Celanese Corporation, New York, N.Y.

[21] Appl. No.: 65,256

[22] Filed: Aug. 9, 1979

[51] Int. Cl.³ .................... B01J 27/14; B01J 29/00
[52] U.S. Cl. .......................... 252/435; 252/437; 252/454
[58] Field of Search .................. 252/435, 437, 454

[56] References Cited

U.S. PATENT DOCUMENTS

| 3,193,511 | 7/1965 | Cramer et al. | 252/453 |
|---|---|---|---|
| 3,341,471 | 9/1967 | Callahan et al. | 252/454 X |
| 3,415,886 | 12/1968 | McClellan | 252/437 X |
| 3,454,630 | 7/1969 | Yamaguchi et al. | 252/546 |
| 3,778,386 | 12/1973 | Takenaka et al. | 252/432 |
| 4,077,912 | 3/1978 | Dolhyj et al. | 252/461 |

Primary Examiner—Delbert E. Gantz
Assistant Examiner—William G. Wright
Attorney, Agent, or Firm—Linn I. Grim

[57] ABSTRACT

Olefin oxidation catalysts having improved attrition resistance are produced by incorporating a substantially uniform-appearing coating of a partially calcined catalytic material onto an inert porous support containing sorbed aqueous silica sol and then completing the calcination of the catalyst. Such catalysts are useful in a variety of exothermic chemical processes, including vapor phase oxidation of olefinically unsaturated hydrocarbons to the corresponding unsaturated aldehydes, especially propylene to acrolein.

8 Claims, 2 Drawing Figures

ATTRITION RESISTANT CATALYSTS

BACKGROUND OF THE INVENTION

The present invention relates to improved fixed bed attrition resistant catalysts and to their use in exothermic chemical processes, such as vapor phase oxidation of olefinically unsaturated hydrocarbons to their corresponding unsaturated aldehydes, particularly propylene to acrolein.

Various oxidation catalysts have been proposed for use in vapor phase catalytic oxidation of olefinically unsaturated hydrocarbons to produce corresponding unsaturated aldehydes with a view towards enhancing catalyst life and selectivity for desired unsaturated hydrocarbon products without reducing rates of conversion of olefin raw material. Such known oxidation catalysts generally contain combinations of alkali metals, alkaline earth metals, V, Cr, Mo, W, Mn, Fe, Co, Ni, Cu, Zn, In, Tl, Sn, Sb, Bi, P, As among other elements.

U.S. Pat. No. 3,454,630 describes a process for converting propylene and isobutylene to the corresponding unsaturated aldehydes and carboxylic acids in the presence of a catalyst of the elements Ni, Co, Fe, Bi, P, Mo and oxygen.

U.S. Pat. No. 3,778,386 describes a vapor phase oxidation process in which propylene can be converted to acrolein utilizing a catalyst containing the following elements on a suitable carrier or binder:

$$Ni_aCo_bFe_cBi_dL_eM_fMo_gO_g$$

wherein Ni, Co, Fe, Bi, Mo and O are the elements nickel, cobalt, iron, bismuth, molybdenum and oxygen, respectively; L is phosphorus, arsenic or boron and M is potassium, rubidium or cesium including mixtures; and wherein a and b are 0 to 15, while a+b is 2 to 15, c is 0.5 to 7, d is 0.1 to 4, e is 0 to 4, f is 12, g is 35 to 85 and h is 0.01 to 0.5. This combination of elements represents a family of highly preferred catalysts for the oxidation of propylene to acrolein.

Generally, catalysts used in the vapor phase oxidation of olefinically unsaturated hydrocarbons have been prepared conventionally as pills or tablets having an essentially uniform distribution of catalyst throughout. Catalysts prepared in the manner can be extremely active when used in fixed bed exothermic oxidation reactions. In some cases, however, "hot spots" can cause large amounts of undesirable by-products to be produced, due to the fact that the heat generated by the reaction cannot be dissipated efficiently by normal heat transfer techniques.

One method which has been tried to overcome this difficulty is to use inert catalyst supports which contain the catalytically active materials coated in or on the support. This reduces the amount of catalytically active material in the reactor and cuts down undesirable catalytic activity, thereby better controlling the heat produced in the reaction and substantially eliminating "hot spots". However, such coated catalysts often exhibit a significant degree of attritability, i.e., they break down in use to give significant amounts of catalyst fines. As these fine particles accumulate in the reactor, high pressure drops develop which must be overcome by applying higher pressures. Once the pressure reaches an unacceptably high level, the reaction must be stopped even though the catalyst may still retain good activity.

Attempts have been made in the past to provide active supported catalysts having acceptable attrition resistance. For example, U.S. Pat. No. 3,341,471 describes attrition resistant solid catalysts prepared by mixing finely divided catalytically active components with an aqueous silica sol, forming a paste or slurry, drying the mixture, heat-treating the finished finely divided catalyst and then pelletizing, yielding a catalyst having catalytically active material fairly uniformly distributed throughout the pellets. This catalyst, however, when used in a fixed bed reactor in reactions such as the oxidation of olefins to oxygenated hydrocarbons, still has a tendency to result in undesirable "hot spots".

U.S. Pat. No. 4,077,912 describes a procedure for producing a coated catalyst on an inert porous support. The catalyst is produced by wetting a porous inert support with an inorganic or organic liquid, water and petroleum ether being specifically disclosed, in such a manner that the resulting wetted support does not have the appearance of free liquid in contact with the support particles, and then gently agitating a catalytically active material onto the wetted support surface. The resulting catalyst is said to have good attrition resistance. The catalytically active material used in this catalyst is the same catalytically active material described in U.S. Pat. No. 3,778,386, earlier discussed. The resulting catalyst, although having good activity and selectivity for the conversion of propylene to acrolein, in many cases has an unacceptably high attrition rate.

In general, the catalysts described in the aforementioned patents have a lower attrition resistance than the catalysts of the present invention.

SUMMARY OF THE INVENTION

We have discovered catalysts for exothermic reactions, especially for the vapor phase oxidation of olefinically unsaturated hydrocarbons to their corresponding unsaturated aldehydes, which exhibit improved attrition resistances and good catalytic activity when employed in such reactions.

Such catalysts are prepared by the following steps:
(1) wetting an inert support with aqueous silica sol;
(2) uniformly coating the outer surface of the wetted porous support with a dried, heat-treated precursor powder of a catalytically active oxide material for the oxidation of olefinically unsaturated hydrocarbons to the corresponding unsaturated aldehydes, and
(3) completely calcining the thus-coated support to provide a stabilized catalyst having the desired catalytic activity for the oxidation of olefinically unsaturated hydrocarbons to the corresponding unsaturated aldehydes.

These catalysts are conveniently prepared and make it possible to conduct strongly exothermic reactions in a fixed bed reactor under better controlled conditions with an extended catalyst lifetime essentially without loss of catalytic reactivity and selectivity.

DETAILED DESCRIPTION OF THE INVENTION

Figure 1:
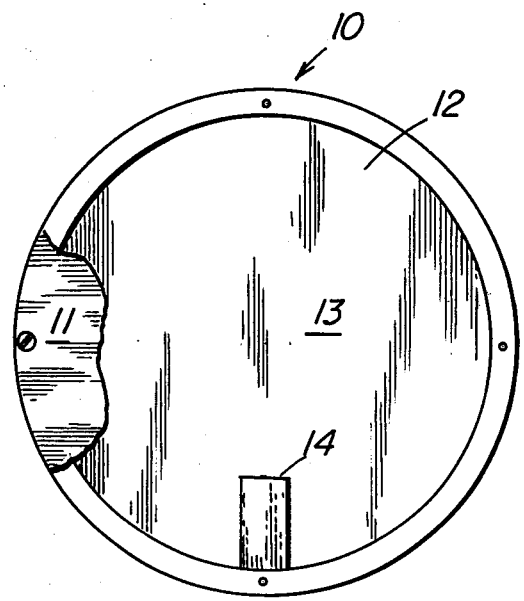

A more detailed description of the preparation of the improved attrition resistant catalysts of the present invention is as follows:
(1) An essentially inert porous support capable of holding finely divided catalytic active material on its outer surface is wetted with a sufficient amount of aqueous silica sol containing from about 20 to about 40 weight percent silica to provide a support which contains up to the maximum amount of aqueous silica sol which the support can sorb without having the appearance of liquid on the outer surface of said support.

(2) The outer surface of the wetted support is coated with a dried precursor of a finely divided catalytically active oxide material for the oxidation of olefinically unsaturated hydrocarbons to the corresponding unsaturated aldehydes to provide a uniformly appearing coating. The precursor, prior to coating, is heated to temperatures from about 200° C. to about 350° C. in the presence of molecular oxygen for a period of time sufficient to remove the majority of the volatiles, i.e., at least 60% volatiles; present therein.

(3) The coated support is then completely calcined at temperatures of from about 400° C. to about 570° C. for a period of time sufficient to provide a thermodynamically stabilized catalyst having the desired catalytic activity for the oxidation conversion of olefinically unsaturated hydrocarbons to the corresponding unsaturated aldehydes.

It is not desirable to completely calcine the precursor of the catalytically active oxide material prior to coating on the aqueous silica sol wetted support and drying the catalyst, since this significantly reduces the activity of the finished catalyst for use in the oxidation of olefinically unsaturated hydrocarbons to the corresponding unsaturated aldehydes.

The essentially inert porous support may be selected from a wide variety of known materials which have an outer surface capable of holding finely divided catalytically active material and which are also capable of being wetted with an aqueous silica sol.

Included among the essentially inert porous supports which can be used in preparing the catalysts of the present invention are alumina, preferably Alundum, a pure crystalline grade of aluminum oxide, silica, alumina-silica, silicon carbide, titania and zirconia. Silicon carbide is especially preferred.

The aqueous silica sol used as the wetting agent for the preparation of the catalysts of this invention is available commercially, or if desired can be derived from water glass or other silicon compounds. The amount of silica in the aqueous silica sol can range from about 20 to about 40 weight percent, based on the total weight of the silica sol, and preferably will range from about 30 to about 40 weight percent, again based on the total weight of the silica sol.

The amount of aqueous silica sol absorbed on the essentially inert porous support can be defined as a percent moisture ratio calculated in the following manner:

% Moisture Ratio = $\dfrac{\text{weight liquid aqueous silica sol}}{\text{weight catalytically active oxide material} + \text{weight liquid aqueous silica sol}} \times 100$ The % moisture ratio can range from about 15% to about 51%, and preferably will range from about 40% to about 50% depending on the essentially inert porous support and the catalytically active oxide material chosen. The amount of aqueous silica sol in the support can contain up to the maximum amount of aqueous silica sol which the support can sorb without having the appearance of liquid on the outer surface of the support. If an excess of silica sol is used, the catalytically active oxide material to be coated onto the support can agglomerate and the resulting catalyst will be undesirable for use in the oxidation process because of high attrition and low oxidation activity. It is highly desirable to wet the support by distributing the aqueous silica sol throughout the support. This can be accomplished by tumbling the wetted support for a short period of time prior to the coating step.

The second component of the catalysts of the present invention is an oxide material which is a catalyst for the oxidation of olefinically unsaturated hydrocarbons to the corresponding unsaturated aldehydes. The preferred catalysts generally contain oxide combinations of alkali metals, alkaline earth metals, V, Cr, Mo, W, Mn, Fe, Co, Ni, Cu, Zn, In, Tl, Sn, Sb, Bi, P, As among other elements. Preferred among these catalytically active oxide materials are the combinations described in U.S. Pat. No. 3,778,386 wherein the catalytically active oxide material has the empirical formula:

$$Mo_{12}Bi_aNi_bFe_cCo_dL_eM_fO_x$$

wherein Mo, Bi, Ni, Fe, Co and O are respectively the elements of molybdenum, bismuth, nickel, iron, cobalt and oxygen; L is at least one element selected from potassium and rubidium; M is at least one element selected from phosphorus, cerium, germanium, manganese, niobium, antimony and tantalum; a, b, c, d, e, f are respectively numbers of atoms of Bi, Ni, Fe, Co, L, M; and wherein a is 0.3–3; b is 1–6; c is 1–6; d is 1–7; e is 0.05 to 2 and f is 0.3–0.6; and x represents the number of oxygen atoms sufficient to satisfy the valence requirements of the other elements. The most preferred catalytic active oxide material has the empirical formula:

$$Mo_{12}BiNi_{2.5}Fe_3Co_{4.5}K_{0.1}P_{0.5}O_x$$

as described in U.S. Pat. No. 4,077,912.

The precursor of the catalytically active oxide material may be prepared by combining the various metals, preferably with a binder. A typical method is generally described in U.S. Pat. No. 3,778,386. The metal compounds can be admixed and slurried in an aqueous medium. Normally it is preferred to incorporate in successive order compounds which are water-soluble or at least partially water-soluble to facilitate formation of the ultimate catalyst's crystalline structure. In a typical preparation of the preferred catalytically active oxide material described hereinbefore, dilute phosphoric acid is added to an aqueous solution of a molybdate compound such as ammonium molybdate. If the physical properties of the particular catalyst are to be enhanced by the addition of a binder material such as Cab-o-Sil, Aerosil or silica sol, at this point in the procedure an appropriate amount of such binder material is stirred into the aqueous medium. The calculated quantities of compounds of cobalt, nickel, iron and bismuth are then successively added to the catalyst preparation medium, preferably in the form of nitrate salts. Addition is facilitated if each of the nitrate compounds is pre-dissolved in water before their successive addition to the catalyst preparation medium. It is advantageous to pre-dissolve the bismuth salt in dilute nitric acid solution before it is added to the preparation medium.

When combining these catalyst components, an insoluble precipitate usually forms upon the addition of the iron nitrate to the catalyst preparation medium. Nonetheless, the successive addition of catalyst components will be continued, using water-soluble compounds of potassium, such as potassium nitrate or potassium hydroxide.

After the completion of the successive addition of catalyst components, the resultant catalyst preparation medium is concentrated to dryness, such as by spray-drying or by means of a roto-vacuum apparatus. The catalyst precursor solids are recovered and then subjected to a heat treatment at a temperature in the range between about 200°–350° C. preferably from about 225°–270° C. in contact with air to effect partial calcination of the catalyst precursor mass. The period of heat treatment on the average will be in the range between about 1-24 hours preferably 1-6 hours. The heat treatment will be carried out for a period of time sufficient to remove the majority of volatiles, e.g., at least 60% to as high as 90% of the volatiles present. This provides a dried catalyst precursor, but not a catalyst in its thermodynamically stabilized form.

The dried, finely divided catalytically active oxide material precursor is coated onto the wetted inert porous support by adding it to the rotating drum containing the wetted inert porous support until the desired amount of precursor is placed onto the support or until no more precursor is taken up on the support.

The amount of catalytically active oxide precursor coated on the support, described in terms of weight percent loading factor, can range from about 20 to about 50 weight percent, preferably from about 25 to about 40 weight percent.

Weight percent loading factor is calculated in the following manner:

$$\text{Weight Percent Loading Factor} = \frac{\text{Weight of Catalyst Precursor}}{\text{Weight of Catalyst Precursor} + \text{Weight of Support}} \times 100$$

The resulting coated support has a uniformly appearing coating, and is then calcined at a temperature in the range from about 400° C. to about 570° C., preferably in the range from about 450° C. to about 540° C., in the presence of molecular oxygen. The calcination procedure preferably is conducted for a period of time sufficient to provide a catalyst having the desired catalytic activity and an extended catalyst life. The calcination period can be conducted for at least 4 hours, preferably 10 hours or longer. The final product is a dried catalyst ready for use in the oxidation conversion of olefinically unsaturated hydrocarbons to their corresponding unsaturated aldehydes.

The dried catalyst can then be evaluated for particle integrity by conducting a special attrition test. The results of the special attrition test are defined in this specification and claims as a "special attrition index" in terms of percentage loss of fines. The special attrition test procedure requires that the sample be thoroughly dried by placing it in a vacuum desiccator over Drierite (anhydrous calcium sulfate dessicant) for a sufficient period of time, for example 18 to 20 hours, to remove substantially all the moisture present. Prior to testing, the catalyst sample is sieved on a 20 mesh screen to remove any fine particles. A 100 gram sample of dried, sieved catalyst is then rotated in a stainless steel cylindrical drum (6 inches in inner length and 10 inches in inside diameter) at 60 revolutions per minute for 1.5 minutes at room temperature. The drum has a radial baffle attached to one of its cylinder faces and the baffle extends 5.5 inches in the axial direction. Additionally, the baffle is attached to the inner cylinder wall and extends 2 inches in the radial direction. Next, the sample is removed from the drum and again sieved on a 20 mesh screen to remove fines. The material remaining on the screen is weighed. The special attrition index is then calculated as follows:

$$\text{special attrition index (weight percent)} = \frac{\text{original weight} - \text{final weight retained on screen}}{\text{original weight}} \times 100$$

The catalysts of this invention will have special attrition indices which preferably do not exceed 10 weight percent according to this test. These catalysts have stable catalytic activity and physical integrity when used in long term continuous conversion of olefinically unsaturated hydrocarbons to aldehydes under vapor phase oxidation conditions.

The drawings are a diagrammatic illustration of the stainless steel cylindrical drum used to evaluate particle integrity of the catalyst in the above-described test for special attrition index.

Figure 2:
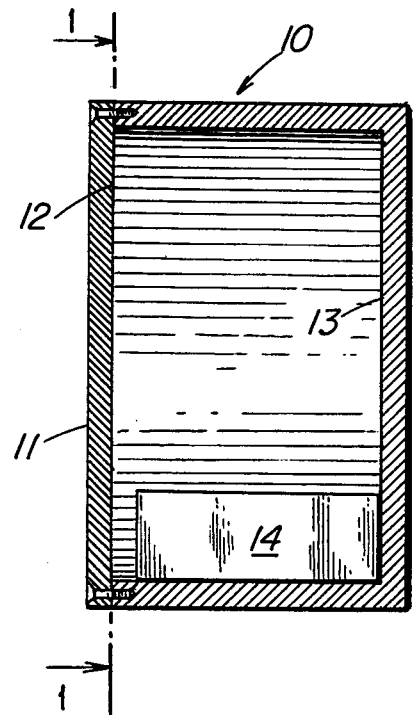

FIG. 1 is a front view of the open cylindrical drum with an indication of a fragmentary portion of the front plate 11. FIG. 2 is a cross section view of the cylindrical drum with cover plate in place. Referring to the drawings, the overall stainless steel cylindrical drum 10 (6 inches in inner length and 10 inches in inside diameter) contains a removable cover 11 on one cylinder face 12. The other cylinder face 13 has a radial baffle 14 attached thereto. The baffle 14 extends 5.5 inches in the axial direction from the inner cylinder face 13. The baffle 14 also is attached to the inner cylinder wall, and is 2 inches wide extending in the radial direction. There are means, not shown, to rotate the stainless steel cylindrical drum 10 at varying speeds.

Catalysts prepared in accordance with this invention can be utilized in the oxidative conversion of olefinically unsaturated hydrocarbons to their corresponding aldehydes, especially propylene to acrolein. The term "olefinically unsaturated hydrocarbons" as employed herein is meant to include alkenes containing between 3 and about 5 carbon atoms as a preferred class of starting materials.

The catalytic oxidation processes of the present invention can be carried out continuously in a fixed bed. Portions of the reactants which do not undergo reaction may be recycled, if desired. The temperatures employed will be preferably between about 300° C. and about 410° C., and more preferably will be in the range of from about 325° C. to about 370° C., especially when oxidizing propylene to acrolein.

The pressures employed in such processes may be subatmospheric, atmospheric or superatmospheric. Usually pressures ranging from 0.5 to 3.0 atmospheres will be utilized, although pressures up to 10 atmospheres and higher may be employed. The contact time of the reactants with catalyst can be between 0.3 and 15 seconds, but is preferably a relatively short time, e.g., from 0.5 to 10 seconds. Contact time means contact time adjusted to 25° C. and atmospheric pressure (conditions denoted by NTP), and is calculated by dividing the volume of the catalyst bed (including voids) by the volume per unit time flow rate of the reactants at NTP.

The oxygen necessary as a reactant in such oxidation processes may be from any molecular oxygen-containing gas, such as concentrated molecular oxygen or air. The molecular oxygen can be mixed in varying amounts with an inert diluent gas, such as nitrogen, argon or carbon dioxide. The unsaturated reactant may be premixed with the molecular oxygen-containing gas before introduction to the reaction zone, or the reactants may be introduced separately into the reaction zone. Also, the unsaturated reactant and/or molecular oxygen-containing gas may be introduced into the reaction zone at one or a plurality of points along the length of the reaction zone. The reactants may be pretreated before entering the reaction zone to remove undesirable components therefrom.

In conducting the oxidation reaction, the gaseous feed mixture should generally contain from 1 to 7 moles of oxygen per mole of the olefinically unsaturated hydrocarbon although the preferred range is from 1.7 to 5.0 moles of oxygen per mole of olefinically unsaturated hydrocarbon. Water is also desirably present in the gaseous feed in amounts of from 1 to 25 moles, and preferably 2 to 20 moles, per mole of unsaturated hydrocarbon. In addition to water, diluents which are gaseous under the reaction conditions and are realtively inert may be introduced into the system. Suitable diluents include nitrogen, flue gas, $CO_2$ and paraffinic hydrocarbons.

The following examples are further illustrative of the present invention. The reactants and other specific ingredients are presented as being typical, and various modifications can be devised in view of the foregoing disclosure within the scope of the invention.

EXAMPLE 1

Silicon carbide spheres of 3/16 inch diameter having a surface area of 0.003 $m^2/g$, a packing density of 40 pounds per cubic foot, a water absorbtivity of 54 weight percent, a total porosity (by mercury penetration) of 0.53 cc/gm and a mdian pore diameter of 78 micrometers were used as the support. 700 grams of these spheres were weighed in a 2 gallon (7-inch diameter) polyethylene jug which was then placed on a jar mill roller (Norton Jar Mill Roller, Model 753 RMV), rotating at 60 revolutions per minute. While the jar was rotating, 402 grams of an aqueous, ammonia stabilized silica sol containing 40% by weight of silica (du Pont Ludox As-40) stabilized to a pH of 8.0 with ammonium hydroxide, was sprayed by a common household sprayer onto the silicon carbide spheres. The moistened spheres were tumbled for 20 minutes to distribute the silica sol throughout the spheres, after which they were transferred to a "V" blender (Patterson Kelley Co. liquid solids 2 quart "V" type).

The catalytically active oxide material to be coated onto the support had the empirical formula:

$Mo_{12}BiNi_{2.5}Fe_3Co_{4.5}K_{0.1}P_{0.5}O_x$ containing 82% catalytically active material and 18% $SiO_2$. This material, including its precursor, was prepared in the manner described in U.S. Pat. No. 3,778,386.

The precursor, after preparation, was heat treated in the presence of molecular oxygen at 260° C. for 2 hours and then added in an amount of 100 grams to the "V" blender containing the wetted spheres. The blender was rotated eight revolutions. Two more 100 gram increments of precursor product were added, with eight revolutions of the blender being made after each addition. Then, a final 100 gram increment (400 grams total) of precursor product was added and the blender rotated for seven minutes. The loading factor of catalyst coating on the support was 36 weight percent and the moisture ratio was 50 weight percent. The coated spheres were calcined for 5 hours at 500° C. in an oven with forced air circulation. The special attrition index of this dried and calcined catalyst, determined as heretofore described, was 5 weight percent.

This catalyst was then used to oxidize propylene to acrolein and acrylic acid in a 0.622 internal diameter reactor tube. The amount of catalyst charged was 15 $cm^3$. The reactor feed composition contained the following mole ratios:

| water to propylene | 5/1 |
| oxygen to propylene | 2.1/1 |
| nitrogen to propylene | 7.8/1 |

The processing conditions used in the reactor and product data are indicated in Table I below:

TABLE I

| Reaction Temp. °C. | Contact Time (NTP) Seconds | Pressure psig | Propylene Conversion % | Yields | | Selectivity | |
| --- | --- | --- | --- | --- | --- | --- | --- |
| | | | | Acrolein % | Acrylic Acid % | Acrolein % | Acrylic Acid % |
| 350 | 2.09 | 15 | 78 | 66 | 1 | 84 | 1 |
| 350 | 2.09 | 15 | 83 | 69 | 5 | 83 | 6 |
| 382 | 2.09 | 15 | 90 | 66 | 9 | 73 | 10 |
| 389 | 2.09 | 15 | 91 | 64 | 11 | 70 | 12 |
| 392 | 2.09 | 15 | 92 | 63 | 11 | 70 | 12 |

In these examples, the terms "conversion", "yield" and "selectivity" are defined as follows:

$$\text{conversion \%} = \frac{\text{moles propylene converted}}{\text{moles propylene fed}} \times 100$$

$$\text{yield mole \%} = \frac{\text{moles acrolein or acrylic acid produced}}{\text{moles propylene fed}} \times 100$$

$$\text{selectivity \%} = \frac{\text{moles acrolein or acrylic acid produced}}{\text{moles of propylene fed-moles unreacted propylene}} \times 100$$

The catalyst with a low attrition index produced by the procedure of this example provides a good activity and selectivity in the oxidation of propylene to acrolein. This catalyst is representative of the catalysts of the present invention.

EXAMPLE 2

300 Grams of the silicon carbide spheres as used in Example 1 were placed in a 2 gallon plastic bottle. The bottle was placed on a Norton Jar Mill rotating at 60 revolutions per minute. Aqueous silica sol (40% silica) in an amount of 75 grams was sprayed on the spheres and the wet spheres were tumbled for 5 minutes.

The precursor of the catalytically active oxide material used in this example is the same as the material described in Example 1 except that this example's precursor was not heat treated after preparation.

The non-heat treated precursor was coated onto the silicon carbide spheres in three increments. First, 67 grams of non-heat treated powder was added to the plastic bottle containing the wetted spheres and rotated for one minute. An additional 15 grams of aqueous silica sol was sprayed onto the spheres and the bottle rotated for another minute. A second increment of 67 grams of non-heat treated precursor was then added to the bottle, and the bottle rotated for four minutes. An additional 5 grams of aqueous silica sol was then sprayed onto the spheres and the bottle rotated for an additional one minute. The final increment of 67 grams of non-heat treated precursor was then added, and the bottle rotated for 4 additional minutes. The resulting product had a catalyst coating loading factor of 40 weight percent and the catalytic ingredients had a moisture ratio of 27 weight percent. The coated product was then calcined for 5 hours at 500° C. in a forced air circulation oven. The special attrition index of the resulting catalyst was 13%. Using the same procedure as used in Example 1 for the oxidation of propylene to acrolein, the following results were obtained using the conditions described in Table II.

EXAMPLE 4

The catalyst procedure of Example 1 was followed with the following exceptions: (1) an 800 gram sample of the precursor of the catalytically active oxide material was heated in the presence of molecular oxygen at 260° C. for 3 hours, then mixed with 160 grams of the same precursor which had been heated in the presence of molecular oxygen at 260° C. for 2 hours; (2) the catalyst product prior to calcination was rotated for 25 minutes instead of 7 minutes; (3) 330 grams of aqueous silica sol (40% silica) were used to spray the silicon carbide spheres, resulting in a moisture ratio of 45% instead of 50%. The special attrition index of the thus-produced catalyst was 8%. Using the same procedure as described in Example 1 for the oxidation of propylene to acrolein, the following results were obtained using the conditions described in Table III.

TABLE III

| Reaction Temp. °C. | Contact Time (NTP) Seconds | Pressure psig | Propylene Conversion % | Yields | | Selectivity | |
|---|---|---|---|---|---|---|---|
| | | | | Acrolein % | Acrylic Acid % | Acrolein % | Acrylic Acid % |
| 350 | 2.09 | 15 | 64 | 54 | 1.8 | 86 | 3 |
| 377 | 2.09 | 15 | 90 | 69 | 8 | 77 | 9 |
| 385 | 2.09 | 15 | 92 | 67 | 10 | 73 | 11 |

The catalyst of Example 4 is a satisfactory catalyst in regard to activity, selectivity and attrition index.

EXAMPLE 5

The catalyst preparation procedure of Example 4 was followed with the exception that the catalyst product prior to calcination was tumbled for 40 minutes. The special attrition index of the finished catalyst was 13%. The reason for the high attrition index appears related to the length of time the catalytically active oxide precursor material was tumbled with the silicon carbide spheres wetted with aqueous silica sol. Rotation for 40

TABLE II

| Reaction Temp. °C. | Contact Time (NTP) Seconds | Pressure psig | Propylene Conversion | Yields | | Selectivity | |
|---|---|---|---|---|---|---|---|
| | | | | Acrolein % | Acrylic Acid % | Acrolein % | Acrylic Acid % |
| 350 | 1.96 | 15 | 57 | 47 | 1 | 82 | 2 |
| 385 | 1.96 | 15 | 75 | 59 | 3 | 79 | 4 |

In Example 2, utilizing a non-heat treated precursor in the coating procedure, a catalyst having an attrition index of 13% is produced which has poorer activity and selectivity than the catalyst of Example 1.

EXAMPLE 3

The catalyst preparation procedure of Example 1 was followed with the exception that 316 grams of water on the same volume basis was used in place of aqueous silica sol, and after the final increment of precursor product was added to the support, the resulting product was blended for 9 minutes. This procedure is similar to the procedure described in U.S. Pat. No. 4,077,912. The resulting catalyst was very weak physically with the majority of the catalyst coating falling off while handling. Because of its physical weakness, a special attrition index could not be determined on this catalyst.

minutes apparently permits too much of the aqueous silica sol to leave the silicon carbide spheres, and seems to give an excess of the aqueous silica sol distributed throughout the precursor coating. This in turn apparently weakens the coating and led to the higher attrition index as compared to that of the catalyst produced in Example 4 (rotated for 25 minutes).

EXAMPLE 6

The catalyst preparation procedure of Example 4 was followed with the following exceptions: the catalyst product prior to calcination was placed in a dry room for 48 hours; the catalyst was calcined for 5 hours at 470° C.; and 350 grams of aqueous silica sol (40% silica) was used to spray the silicon carbide spheres, resulting in a moisture ratio of 46.7% instead of 45%. The special attrition index of the finished catalyst was 13.5%. The reason for the high attrition index may relate to the time the precursor was tumbled with the wetted silicon carbide spheres, combined with the long delay before calcination. The oxidative activity of this catalyst was satisfactory but the special attrition index was not in the preferred range.

EXAMPLE 7

The catalyst preparation procedure of Example 6 was repeated except that the precursor was rotated with the wetted silicon spheres for only 7 minutes and 402 grams of aqueous silica sol (40% silica) was used to spray the silicon carbide spheres, resulting in a moisture ratio of 49.9% instead of 46.7%. The special attrition index was 4.5%.

What is claimed is:

1. A catalyst for the oxidative conversion of olefinically unsaturated hydrocarbons to the corresponding unsaturated aldehydes having improved attrition resistance prepared by the steps comprising:
   (1) wetting an essentially inert porous support capable of holding finely divided catalytically active oxide material on its outer surface with a sufficient amount of aqueous silica sol containing from about 20 to about 40 weight percent silica, based on the weight of the aqueous silica sol to provide a wetted support which contains up to the maximum amount of aqueous silica sol which the support can sorb without having the appearance of liquid on the outer surface of said wetted support;
   (2) coating the outer surface of said wetted support with a uniformly appearing coating of a dried precursor of a finely divided catalytically active oxide material for the oxidation of olefinically unsaturated hydrocarbons to the corresponding unsaturated aldehydes, said precursor having been previously heated at a temperature of from about 200° C. to about 350° C. in the presence of molecular oxygen to remove the majority of the volatiles therefrom;
   (3) calcining said coated wetted support at a temperature of from about 400° C. to about 570° C. for a period of time sufficient to provide a catalyst having the desired catalytic activity and an extended catalyst life.

2. A catalyst as described in claim 1 having a special attrition index not exceeding about 10 weight percent.

3. A catalyst as described in claim 2 wherein said inert porous support is silicon carbide, the aqueous silica sol used contains 30 to 40 weight percent of silica, the amount of catalytically active oxide material used ranges from a loading factor of about 20 to about 50 weight percent, the percent moisture ratio ranges from about 40 to about 51 percent, and the calcining temperature ranges from about 450° C. to 540° C.

4. A catalyst as described in claim 3 wherein the coated wetted support is calcined at a temperature in the range of from about 450° C. to about 540° C. and the amount of catalytically active oxide material used ranges from a loading factor of about 25 to about 40 weight percent.

5. A catalyst as described in claim 4 wherein the catalytically active oxide material has the empirical formula:

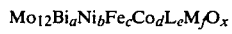

$$Mo_{12}Bi_aNi_bFe_cCo_dL_eM_fO_x$$

wherein Mo, Bi, Ni, Fe, Co and O are respectively the elements of molybdenum, bismuth, nickel, iron, cobalt and oxygen; L is at least one element selected from potassium and rubidium; M is at least one element selected from phosphorus, cerium, germanium, manganese, niobium, antimony and tantalum; a, b, c, d, e, f are respectively number of atoms of Bi, Ni, Fe, Co, L, M; wherein a is 0.3–3; b is 1–6; c is 1–6; d is 1–7; e is 0.05 to 2 and f is 0.3–0.6; and x represents the number of oxygen atoms sufficient to satisfy the valence requirements of the other elements.

6. A catalyst as described in claim 5 wherein the catalytically active oxide material has the empirical formula:

$$Mo_{12}BiNi_{2.5}Fe_3Co_{4.5}K_{0.1}P_{0.5}O_x$$

7. A process for producing an improved attrition resistant catalyst for the oxidative conversion of olefinically unsaturated hydrocarbons to the corresponding aldehydes comprising the steps of:
   (1) wetting an essentially inert porous support capable of holding finely divided active catalytic material on its outer surface with a sufficient amount of aqueous silica sol containing from about 20 to about 40 weight percent silica, based on the weight of the aqueous silica sol to provide a wetted support which contains up to the maximum amount of aqueous silica sol which the support can sorb without having the appearance of liquid on the outer surface of said wetted support;
   (2) coating the outer surface of said wetted support with a uniformly appearing coating of a dried precursor of a finely divided catalytically active oxide material for the oxidation of olefinically unsaturated hydrocarbons to the corresponding unsaturated aldehydes, said precursor having been heated at a temperature of from about 200° C. to about 350° C. in the presence of molecular oxygen for a period of time sufficient to remove the majority of the volatiles therefrom; and
   (3) calcining said coated wetted support at a temperature of from about 400° C. to 570° C. to provide a thermodynamically stabilized catalyst having the desired catalytic activity.

8. A process as described in claim 7 wherein said coated wetted support is dried prior to being calcined.

* * * * *